United States Patent
Kang et al.

(10) Patent No.: US 8,340,246 B2
(45) Date of Patent: Dec. 25, 2012

(54) X-RAY IMAGING APPARATUS AND METHOD FOR REDUCING X-RAY SCATTERING

(75) Inventors: Dong-Goo Kang, Suwon-si (KR);
Seong-Deok Lee, Suwon-si (KR);
Young-Hun Sung, Hwaseong-si (KR);
Jong-Ha Lee, Hwaseong-si (KR);
Sung-Su Kim, Yongin-si (KR);
Seok-Min Han, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 237 days.

(21) Appl. No.: 12/842,134

(22) Filed: Jul. 23, 2010

(65) Prior Publication Data
US 2011/0019798 A1 Jan. 27, 2011

(30) Foreign Application Priority Data
Jul. 23, 2009 (KR) .................. 10-2009-0067389

(51) Int. Cl.
*G01N 23/083* (2006.01)
*G21K 5/10* (2006.01)
*H05G 1/64* (2006.01)

(52) U.S. Cl. .................. 378/62; 378/98.8; 378/146

(58) Field of Classification Search .............. 378/62, 378/91, 98.8, 145, 146, 196, 197
See application file for complete search history.

(56) References Cited

U.S. PATENT DOCUMENTS

| | | | | | |
|---|---|---|---|---|---|
| 5,058,190 | A | * | 10/1991 | Levitt et al. | 382/324 |
| 5,530,935 | A | * | 6/1996 | Dillen | 378/98.2 |
| 5,887,049 | A | * | 3/1999 | Fossum | 378/98.8 |
| 6,115,447 | A | | 9/2000 | Hsieh | |
| 6,173,033 | B1 | * | 1/2001 | Klingenbeck-Regn et al. | 378/20 |
| 6,208,710 | B1 | * | 3/2001 | Nagai | 378/108 |
| 6,215,848 | B1 | * | 4/2001 | Linders et al. | 378/98.12 |
| 6,249,003 | B1 | * | 6/2001 | Culp | 250/363.04 |
| 6,292,534 | B1 | * | 9/2001 | Linders et al. | 378/98.2 |
| 6,307,915 | B1 | * | 10/2001 | Frojdh | 378/98.8 |
| 6,339,636 | B1 | * | 1/2002 | Ogawa | 378/146 |
| 6,404,852 | B1 | * | 6/2002 | Petrick et al. | 378/98.8 |
| 6,404,854 | B1 | * | 6/2002 | Carroll et al. | 378/98.8 |
| 6,674,837 | B1 | * | 1/2004 | Taskar et al. | 378/122 |
| 6,797,960 | B1 | * | 9/2004 | Spartiotis et al. | 250/370.09 |
| 6,917,041 | B2 | * | 7/2005 | Doty et al. | 250/370.09 |

(Continued)

FOREIGN PATENT DOCUMENTS
JP  11-197145  7/1999
KR  10-2006-0050407  5/2006

*Primary Examiner* — Allen C. Ho
(74) *Attorney, Agent, or Firm* — NSIP Law (57) ABSTRACT

An X-ray imaging apparatus and method for reducing X-ray scattering are provided. The X-ray imaging apparatus includes an X-ray source, a collimator, a detector, and a controller. The X-ray source emits X-rays, the collimator collimates the X-rays into an X-ray beam, and the detector may include a two-dimensional array of pixels. The controller controls the collimator such that the X-ray beam scans a subject while moving over time. In addition, the controller operates the detector to only operate pixels at an exposure area of the detector where the X-ray beam arrives without scattering such that photocharges generated due to the X-ray exposure can be accumulated and stored in the pixels.

19 Claims, 9 Drawing Sheets

U.S. PATENT DOCUMENTS

| | | |
|---|---|---|
| 7,010,091 B2 * | 3/2006 | Hayashida et al. .......... 378/98.8 |
| 7,200,201 B2 * | 4/2007 | Unger et al. .................... 378/62 |
| 7,340,033 B2 | 3/2008 | Mollus et al. |
| 7,508,903 B2 | 3/2009 | Nishide et al. |
| 7,978,816 B2 * | 7/2011 | Matsuura et al. ............... 378/62 |
| 8,005,187 B2 * | 8/2011 | Suzuki et al. ................... 378/39 |
| 2004/0120457 A1 | 6/2004 | Karellas et al. |
| 2005/0008121 A1 | 1/2005 | Low et al. |

* cited by examiner

X-RAY IMAGING APPARATUS AND METHOD FOR REDUCING X-RAY SCATTERING

CROSS REFERENCE TO RELATED APPLICATION(S)

This application claims the benefit under 35 U.S.C. §119 (a) of Korean Patent Application No. 10-2009-0067389, filed on Jul. 23, 2009, in the Korean Intellectual Property Office, the entire disclosure of which is incorporated herein by reference for all purposes.

BACKGROUND

1. Field

The following description relates to an X-ray imaging system, and more particularly, to an X-ray imaging apparatus and method for reducing X-ray scattering.

2. Description of the Related Art

In a medical imaging system, X-ray radiation arrives at a detector such as a photo-detective film or a photo detector and is categorized into attenuated primary radiation and scattered radiation. Generally, the primary radiation forms an image, and the scattered radiation deteriorates the image quality. Typically, an anti-scatter grid is interposed between a patient and the detector and is used to allow most of the primary radiation to pass therethrough and to attenuate scattered radiation.

The anti-scatter grid may include inter-space materials deposited in parallel, such as strips of lead foil, solid polymer materials, fiber composite materials, and the like. However, such anti-scatter grids cannot thoroughly remove the scattered radiation, and in addition the grids often absorb a portion of the primary radiation. The result of this is that less primary radiation reaches a subject during imaging causing a loss in quality of an image. Moreover, when using the anti-scatter grid to absorb the primary radiation, high radiation emission is constantly required to maintain a signal-to-noise ratio in a photo-detector at a necessary level, thereby causing an increase in radiation exposure to a patient and an increase in power consumption.

SUMMARY

In one general aspect, there is provided an X-ray imaging apparatus comprising: an X-ray source configured to emit X-rays; a collimator configured to collimate X-rays into an X-ray beam; a detector comprising a two-dimensional array of pixels configured to accumulate and store photocharges; and a controller configured to: control the collimator such that the X-ray beam scans a subject while moving over time; and control the detector to only operate pixels at an exposure area of the detector where the X-ray beam arrives without scattering such that photocharges generated due to X-ray exposure are accumulated and stored in the pixels.

The X-ray imaging apparatus may further include that the controller is further configured to control the detector to output signals corresponding to the photocharges stored in the pixels when the scanning of the subject or a predetermined area of the subject is completed.

The X-ray imaging apparatus may further include that the controller comprises an image processor configured to generate an image by processing the signals corresponding to the photocharges accumulated in the detector.

The X-ray imaging apparatus may further include that the accumulated photocharges are retained in the pixels until the signals corresponding to the accumulated photocharges are output.

The X-ray imaging apparatus may further include that the detector comprises a complementary metal-oxide semiconductor (CMOS) image device.

The X-ray imaging apparatus may further include that each pixel comprises: a photodiode configured to: receive the X-ray beam; and generate the photocharge; a transmission transistor that is connected to the photodiode and configured to transmit the photocharge; a transmission control transistor configured to control the transmission transistor; a floating diffusion node configured to receive the photocharge through the transmission transistor; a reset transistor configured to discharge the photocharge accumulated in the floating diffusion node; a source follower transistor that amplifies and converts the photocharge in the floating diffusion node into a voltage signal; and a selection transistor configured to selectively output the voltage signal.

The X-ray imaging apparatus may further include that, in each pixel: a column selection signal connected to a drain end of the transmission control transistor, a gate signal of the transmission control transistor, and a reset signal applied to the reset transistor are set to an increased level such that photocharges accumulated in the photodiode and the floating diffusion node are discharged immediately before exposure to the X-ray radiation starts; and the gate signal of the transmission control transistor and the column selection signal are set to an increased level such that the photocharge accumulated in the photodiode is transferred to the floating diffusion node at end of exposure to the X-ray radiation.

The X-ray imaging apparatus may further include that: the detector comprises a sensor configured to recognize an X-ray arrival location in real-time; and the controller is further configured to operate pixels positioned at the X-ray arrival location based on the recognized X-ray arrival location.

The X-ray imaging apparatus may further include that two or more X-ray beams are simultaneously emitted towards the subject.

In another general aspect, there is provided an X-ray imaging method, comprising: radiating an X-ray beam towards a subject while moving the X-ray beam over time; operating pixels in an exposure area where the X-ray beam arrives without scattering; accumulating photocharges generated due to X-ray radiation exposure in the pixels over time; and outputting signals corresponding to the photocharges.

The X-ray imaging method may further include that the outputting of the signals corresponding to the photocharges is performed when scanning of the subject or a predetermined area of the subject is completed.

The X-ray imaging method may further include generating an image using the output signals.

The X-ray imaging method may further include that the photocharges accumulated in the pixels are retained in the pixels until image signals corresponding to the photocharges are output.

The X-ray imaging method may further include that two or more X-ray beams are simultaneously emitted towards the subject.

In another general aspect, there is provided a controller for controlling an imaging apparatus, the controller comprising: a source controller configured to control a source to emit a source beam from a start point to an end point to obtain information about a subject; an exposure controller configured to selectively control a detector comprising an array of pixels configured to accumulate and store photocharges over time corresponding to the emitted source beam to obtain information about the subject; and a synchronization controller configured to synchronize the source controller and the exposure controller such that the movement of the source beam is synchronized with the portion of pixels used to detect photocharges as the source beam moves from the start point to the end point, wherein the exposure controller is further configured to control the detector such that only a portion of the pixels detect at the same time and the remaining pixels do not detect.

The controller may further include a collimator controller configured to control the movement of a collimator disposed between the source and the detector such that the movement of the collimator is synchronized with the movement of the source beam.

The controller may further include that the exposure controller is further configured to control a sensor of the detector to sense location information about a location on the array of pixels where the source beam arrives at the detector, in real time.

The controller may further include that the synchronization controller is further configured to synchronize the source controller and the exposure controller based on the sensed location information.

The controller may further include that the synchronization controller is further configured to control the exposure control to predict the location where the source beam arrives over time.

Other features and aspects may be apparent from the following description, the drawings, and the claims.

BRIEF DESCRIPTION OF THE DRAWINGS

Throughout the drawings and the description, unless otherwise described, the same drawing reference numerals should be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein may be suggested to those of ordinary skill in the art. The progression of processing steps and/or operations described is an example; however, the sequence of steps and/or operations is not limited to that set forth herein and may be changed as is known in the art, with the exception of steps and/or operations necessarily occurring in a certain order. Also, descriptions of well-known functions and structures may be omitted for increased clarity and conciseness.

Figure 1:
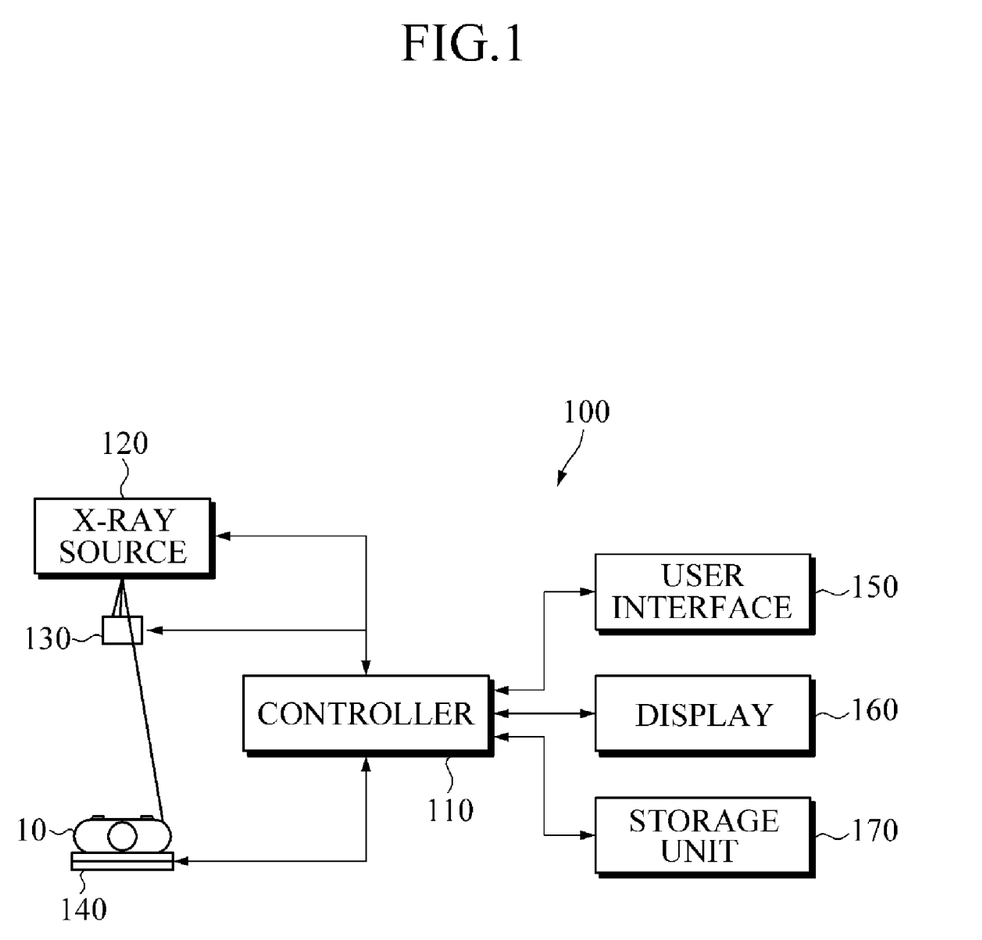
FIG. 1 is a diagram illustrating an example of an X-ray imaging apparatus.

FIG. 1 illustrates an example of an X-ray imaging apparatus. Referring to FIG. 1, the X-ray imaging apparatus 100 includes a controller 110, an X-ray source 120, a collimator 130, a detector 140, a user interface 150, a display 160, and a storage unit 170. The X-ray imaging apparatus 100 may be implemented in various forms, for example, a medical imaging apparatus, a multi-energy material decomposition apparatus, and the like.

The controller 110 may control the X-ray imaging apparatus 100. For example, the controller 110 may control the X-ray source 120, the collimator 130, and the detector 140 to obtain an image and reduce X-ray scattering. The controller 110 may include an image processing module that processes an image signal detected by the detector 140.

The X-ray source 120 emits X-rays. The collimator 130 is disposed between the X-ray source 120 and the detector 140, and collimates the X-rays into an X-ray beam under the control of the controller 110. As described herein, subject 10 is an object to be analyzed based on an X-ray image, for example, a person, an animal, and the like.

The collimator 130 may be an electronically controllable shutter that collimates the X-rays into an X-ray beam of various forms. For example, the collimator 130 may form various forms of X-ray beams such as a pencil beam, a fan beam, a small box-beam, and the like. The collimator 130 may have a plurality of apertures or slots to emit two or more X-ray beams in parallel to each other, towards the subject 10. The parallel emission of the plural X-ray beams may reduce the amount of time for obtaining an X-ray image of the subject 10. The collimator 130 may continuously move under the control of the controller 110 and may emit the X-rays to a particular area of the subject 10 over time.

The detector 140 includes a two-dimensional array of pixels. For example, the detector 140 may drive only those pixels which are positioned corresponding to an exposure area of the subject 10 where the X-ray beam arrives, and may accumulate and store photocharges generated due to X-ray exposure in the pixels. Consequently, the pixels positioned corresponding to the exposure area where the X-ray beam arrives may be exposed to the X-ray radiation. The operation of the detector 140 is further described with reference to FIGS. 2A to 2C.

The user interface 150 receives data or instructions for operation of the X-ray imaging apparatus 100 from a user and transfers it to the controller 110. The display 160 displays an X-ray image processed by the controller 110. The storage unit 170 stores data and applications that may be used for operation of the X-ray imaging apparatus 100. The storage unit 170 may store the X-ray image processed by the controller 110 in a predetermined storing area.

Figure 2A:
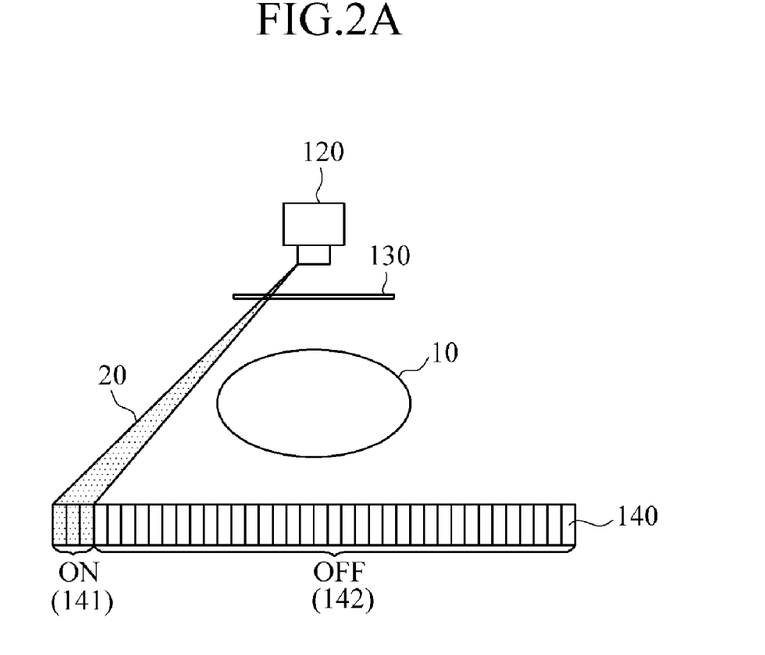
FIGS. 2A through 2C are diagrams illustrating examples of imaging operations of an X-ray imaging apparatus.
Figure 2B:
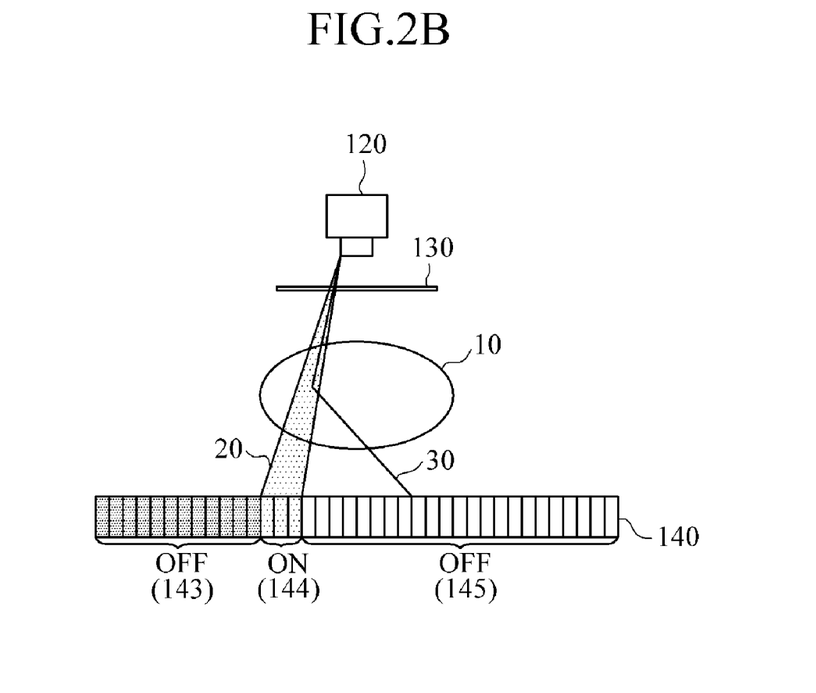
Figure 2C:
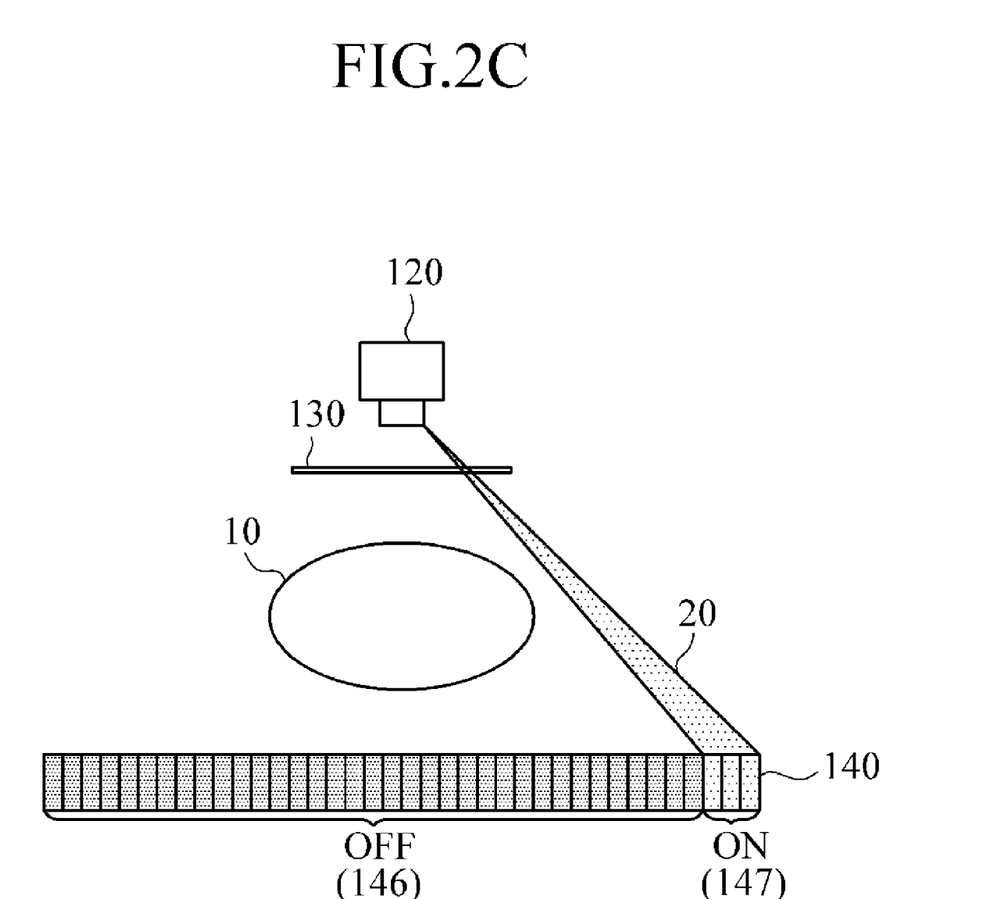

FIGS. 2A through 2C illustrate examples of imaging operations of an X-ray imaging apparatus, for example, the X-ray imaging apparatus 100 of FIG. 1. FIGS. 2A through 2C illustrate how the subject 10 interposed between the detector 140 and the X-ray source 120 may be scanned with X-ray beams over time. In this example, a beam 20 corresponds to a beam of primary radiation and a line 30 corresponds to a scattered X-ray. In the example of FIGS. 2A through 2C, a side view of a two-dimensional pixel array of the detector is illustrated.

Referring to FIG. 2A, an X-ray beam emitted from the X-ray source 120 starts scanning from one end (the left end in FIG. 2A) of the detector 140. Under the control of a controller 110, the detector 140 drives pixels 141 on an area where the beam 20 of primary radiation arrives to accumulate photocharges according to the X-ray irradiation. Pixels 142 of the detector 140 are an area where the beam 20 of primary radiation does not reach.

FIG. 2B illustrates the subject 10 to which the beam 20 of primary radiation is applied over a predetermined period of time after the period of time illustrated in FIG. 2A. In FIG. 2B, the detector 140 only drives the pixels 144 in an area where the beam 20 of primary radiation arrives, and does not drive the remaining pixels 143 and 145. Therefore, even when the scattered X-ray 30 is generated due to the subject 10, the pixels in an area where the beam 30 of scattered radiation arrives are not operated. Accordingly, scattering noise due to the scattered X-ray 30 is reduced in an image signal. The pixels 143 in an area to which the beam 20 of primary radiation was previously applied still retain photocharges accumulated therein until the photocharges are output.

FIG. 2C illustrates the subject 10 a predetermined period of time after the period of time illustrated in FIG. 2B, where the scanning with the beam 20 of primary radiation is almost completed on the subject 10. In this example, only pixels 147 positioned at the right end of the detector 140 where the beam 20 of primary radiation is detected are operated to accumulate photocharges generated due to X-ray radiation exposure. Pixels 146 in an area to which the beam 20 of primary radiation is applied retain the accumulated photocharges until the photocharges are output.

In this example, even without an anti-scatter grid, an X-ray image may be obtained without image artifacts. Additionally, because there is no anti-scatter grid, X-ray beam intensity does not need to be reduced, thereby increasing efficiency of X-ray radiation power and reducing the exposure of a subject to the X-ray radiation. Accordingly, a more safer examination may be realized. Moreover, noise due to scattering may be reduced, an X-ray image containing accurate data may be obtained, and interpretation of the image may be more accurate. Also, noise due to Compton scattering is prevented. Accordingly, a value of X-ray attenuation may be estimated and the X-ray imaging apparatus may benefit a technique such as multi-energy material decomposition using an X-ray image, which requires precise attenuation value information.

Figure 3A:
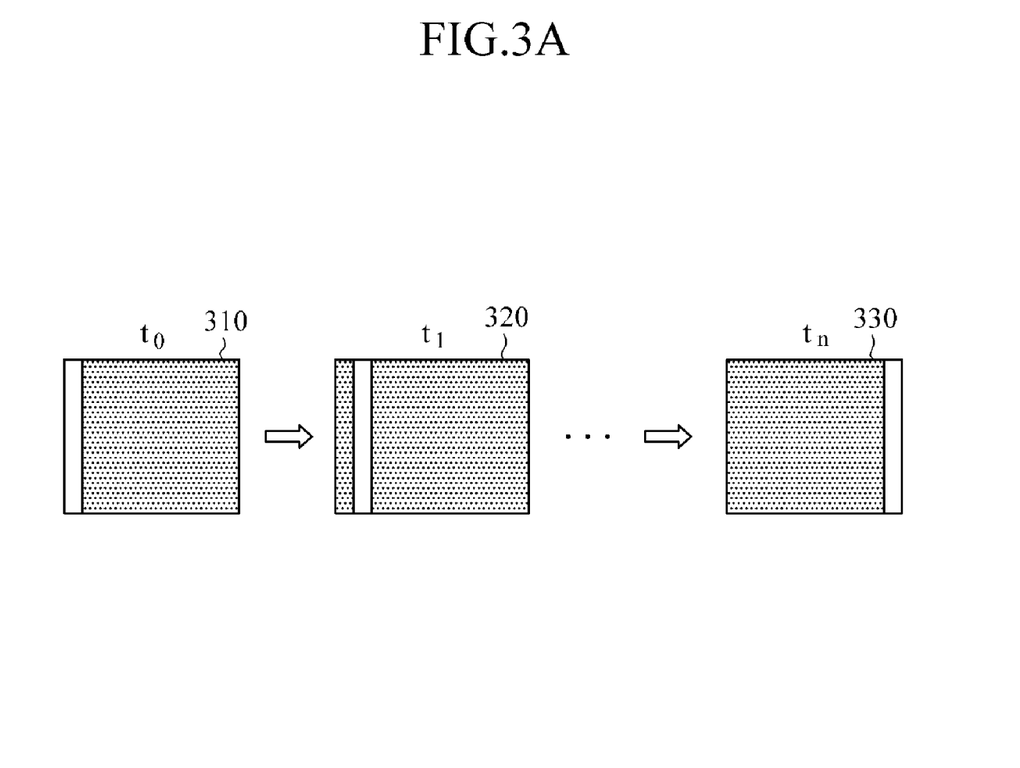
FIG. 3A is a diagram illustrating an example of states of a detector that is exposed to X-ray radiation.
Figure 3B:
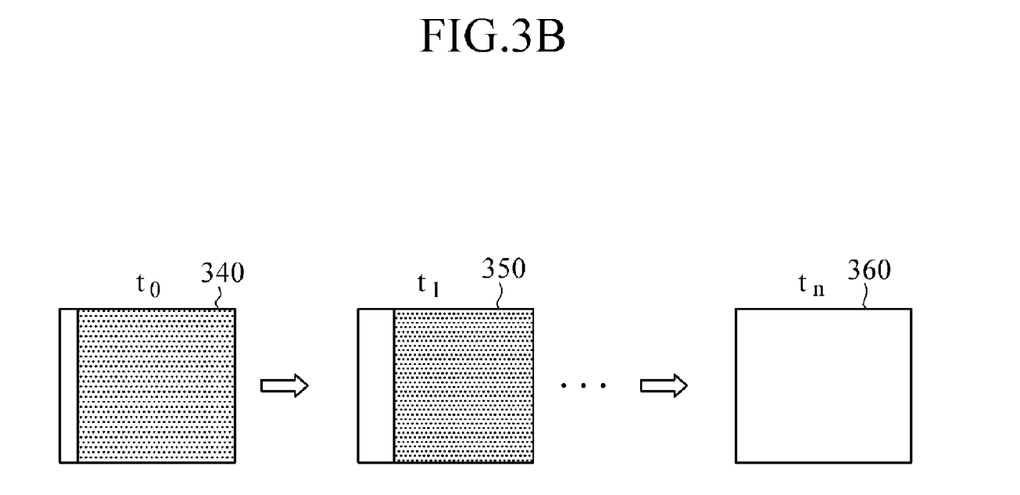
FIG. 3B is a diagram illustrating an example of states of the detector that accumulates photocharges generated due to the X-ray radiation exposure.

FIG. 3A illustrates an example of states of a detector that is exposed to X-ray radiation, and FIG. 3B illustrates an example states of the detector that accumulates photocharges generated due to X-ray radiation exposure.

Referring to FIGS. 3A and 3B, panels 310, 320, 330, 340, 350, and 360 represent changes in states of the a detector over time, for example, detector 140 shown in FIG. 1. In the example shown in FIG. 3A, the white area of each of the panels 310, 320, and 330 corresponds to an area which is exposed to an X-ray beam without scattering, for example, an area at which a beam of primary radiation arrives. In the example shown in FIG. 3B, the white area of each of the panels 340, 350, and 360 corresponds to an area where photocharge accumulation occurs over time according to X-ray radiation exposure.

In FIG. 3A, an X-ray beam traverses the panel 310, 320, and 330 of the detector (see FIGS. 2A to 2C) without scattering from start scanning time $t_0$ to scanning termination time $t_n$.

In FIG. 3B, the panel 340 which corresponds to the panel 310 of FIG. 3A shows that photocharges are accumulated at a start point at time $t_0$ in an area of the pixels corresponding to the white stripe where the X-ray beam arrives, and the panel 350 which corresponds to the panel 320 of FIG. 3A shows that photocharges are accumulated at a mid-point at time $t_1$ in an area of the pixels corresponding to the white stripe where the X-ray beam has arrived. The panel 360 shows that photocharges have accumulated in all pixels of the detector when the scanning is finished at an end point at time $t_n$.

Figure 4A:
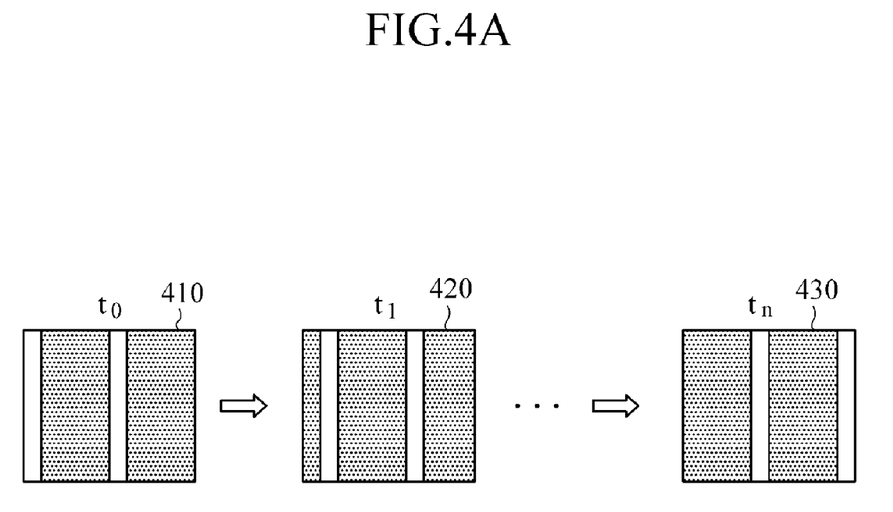
FIG. 4A is a diagram illustrating another example of states of a detector that is exposed to X-ray radiation.
Figure 4B:
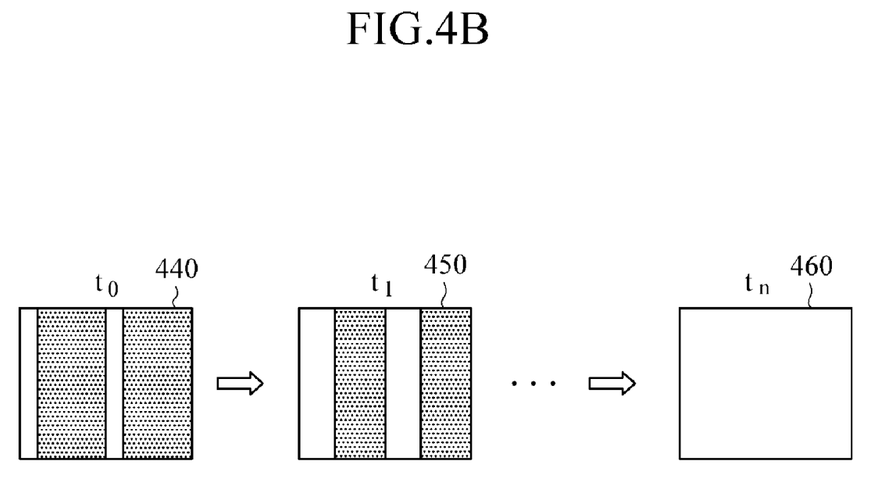
FIG. 4B is a diagram illustrating an example of states of the detector of FIG. 4A in which photocharges generated due to the X-ray radiation exposure are accumulated.

FIG. 4A illustrates another examples of states of a detector that is exposed to X-ray radiation, and FIG. 4B illustrates an example of states of the detector of FIG. 4A on which photocharges generated due to X-ray radiation exposure are accumulated.

Referring to FIG. 4A, in this example a collimator includes a pair of apertures to emit a pair of X-ray beams. In FIG. 4A, panels 410, 420, and 430 represent the states of the detector at $t_0$, $t_1$, and $t_n$, respectively, where the pair of X-ray beams traverse the detector without scattering.

In FIG. 4B, the panel 440 which corresponds to the panel 410 of FIG. 4A shows that photocharges are accumulated at $t_0$, in an area of the pixels corresponding to the white stripe where the pair of X-ray beams arrive, and the panel 450 which corresponds to the panel 420 of FIG. 4A shows that photocharges are accumulated at $t_1$, in an area of the pixels corresponding to the white stripe where the X-ray beams have traversed. The panel 460 shows that photocharges have accumulated on all pixels of the detector at $t_n$ when the scanning is completed.

As such, when a plurality of X-ray beams are used for scanning, scanning time may be reduced as well as the time it takes for the detector to output pixel signals. Thus, changes of photocharges accumulated in the pixels may be prevented such that the photocharges corresponding to accumulation only when the pixels are exposed to X-ray radiation may be more accurately detected.

Figure 5:
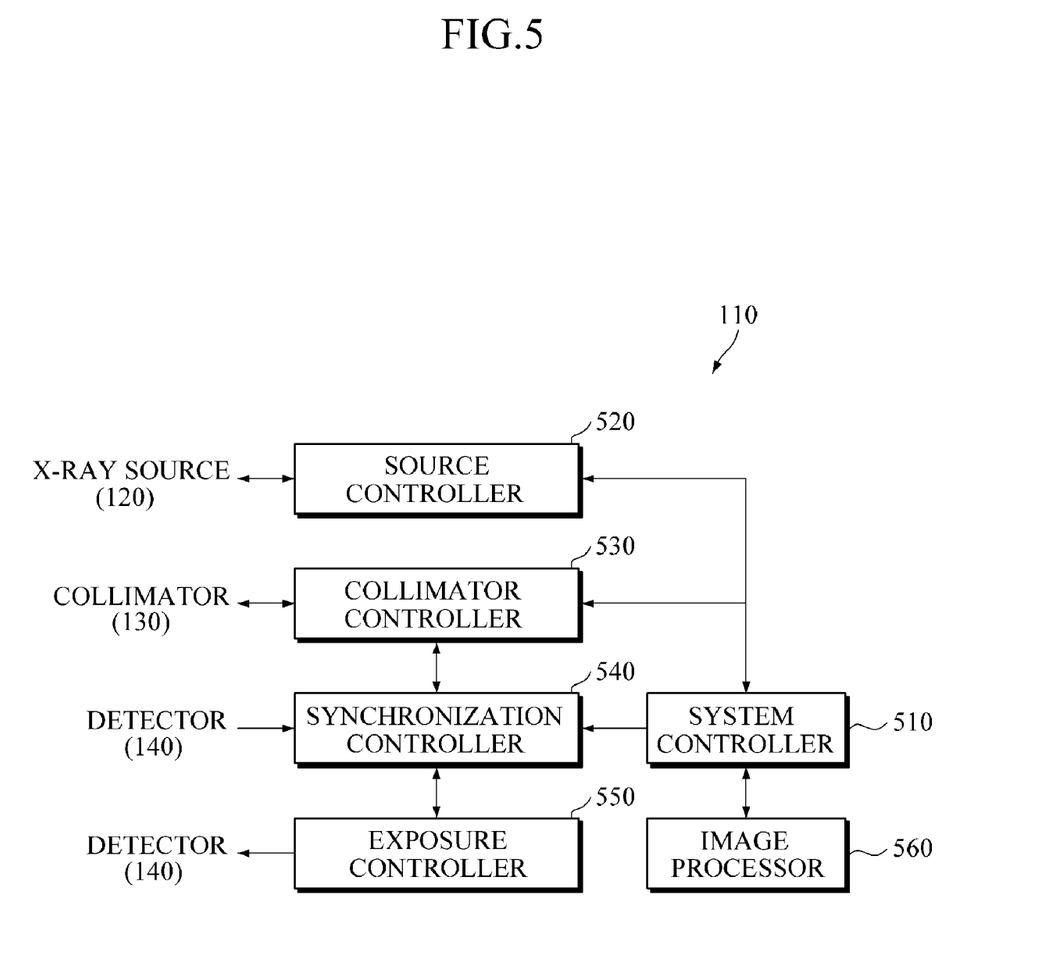
FIG. 5 is a diagram illustrating an example of a controller that may be included in an X-ray imaging apparatus.

FIG. 5 illustrates an example of a controller that may be included in an X-ray imaging apparatus, for example, the X-ray imaging apparatus 100 of FIG. 1.

In this example, controller 110 includes a system controller 510, a source controller 520, a collimator controller 530, a synchronization controller 540, an exposure controller 550, and an image processor 560.

The system controller 510 provides general control of data receipt/transmission between elements included in the controller 110. The source controller 520 controls the X-ray source 120 to emit a sufficient amount of X-rays to obtain information about the subject 10 (see FIG. 1). The source controller 520 maintains the X-ray source 120 in an on state such that X-ray radiation emission continues until scanning of the subject 10 is completed.

The image processor 560 uses signals output from the detector 140 (see FIG. 1) to create an image, and performs general post-processing of the image such as noise reduction and color adjustment.

The collimator controller 530 and the exposure controller 550 control the collimator 130 and the detector 140, respectively, under the control of the synchronization controller 540. The collimator controller 530 may adjust the aperture of the collimator 130 to form an X-ray beam of a predetermined form. The collimator controller 530 may control the movement of the collimator 130 such that the subject 10 may be scanned with the X-ray beam from the collimator 130. The exposure controller 550 provides a signal for operating the pixels of the detector 140, and controls the detector 140 to selectively drive the pixels at an area where the X-ray beam arrives without scattering such that photocharges generated due to the X-ray radiation exposure are accumulated in the pixels.

The synchronization controller 540 controls the collimator controller 530 and the exposure controller 550 to be synchronized with each other. Accordingly, only an area of pixels where the X-ray beam passes through the collimator 130 and arrives at the detector 140 are driven and photocharges corresponding to the X-ray radiation are accumulated on the pixels.

The synchronization controller 540 may control the exposure controller 550 to predict the X-ray scanning location over time from the start of scanning to the termination of the scanning and to drive pixels positioned at the location predicted at the corresponding time. For example, if the detector 140 includes a sensor that detects the X-ray arrival position in real-time, the synchronization controller 540 may receive information about the detected position in real-time, and control the exposure controller 550 to operate the pixels at the detected position.

Alternatively, the synchronization controller 540 may control the exposure controller 550, with additional reference to an X-ray arrival position received in real-time from the detector 140. Accordingly, the synchronization controller 540 may control the exposure controller 550 to drive pixels at which the X-ray beam of primary radiation arrives while controlling the exposure controller 550 according to the predicted X-ray arrival position. As such, various methods may be used to synchronize the X-ray radiation position with the corresponding operation of the detector 140.

Figure 6:
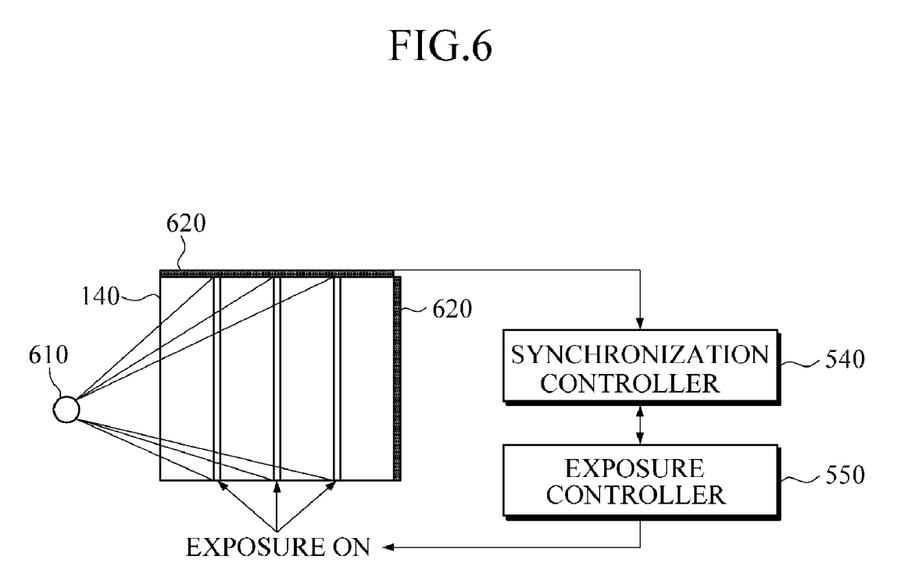
FIG. 6 is a diagram illustrating an example of the operation of a synchronization controller.

FIG. 6 illustrates an example of the operation of a synchronization controller.

Referring to FIG. 6, detector 140 may include an X-ray monitor sensor 620 to monitor in real-time a scanning position to which an X-ray is emitted. The X-ray monitor sensor 620 may be included in a pixel array or may be configured separately. In one example, a currently detected X-ray location obtained by the X-ray monitor sensor 620 may be transmitted to the synchronization controller 540. The synchronization controller 540 may control the exposure controller 550 such that an area of pixels corresponding to the X-ray detected location are driven. Then, the exposure controller 550 may determine an exposure area of the detector 140 corresponding to the current X-ray detected location. Accordingly, the pixels on the exposure area may be driven to accumulate photocharges generated due to the X-ray radiation exposure thereon.

Figure 7:
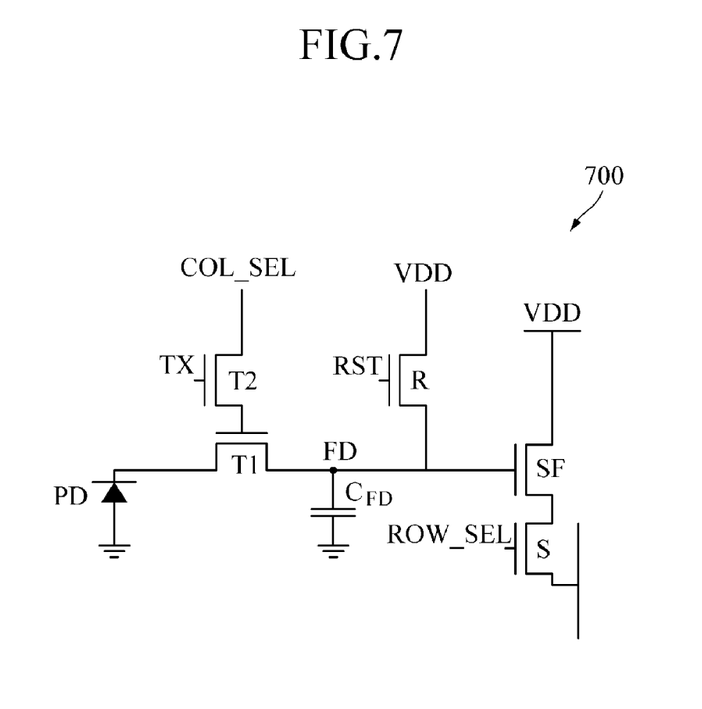
FIG. 7 is a diagram illustrating an example of a pixel included in a pixel array of a detector.

FIG. 7 illustrates an example a pixel included in a pixel array of a detector.

The pixels included in the detector 140 may be, for example, complementary metal-oxide semiconductor (CMOS) devices. Referring to FIG. 7, pixel 700 includes a photodiode PD, a transmission transistor T1, a transmission control transistor T2, a floating diffusion node capacitor $C_{FD}$, a reset transistor R, a source follower transistor SF, and a selection transistor S.

The photodiode PD receives X-ray radiation to generate photocharges.

The pixel 700 further includes a transmission control transistor T2 connected to a gate of the transmission transistor T1, unlike a general transistor structure. The photocharges accumulated in the photodiode PD are transferred to a floating diffusion (FD) node when the transmission control transistor T2 and the transmission transistor T1 are in an ON state.

The floating diffusion node capacitor $C_{FD}$ accumulates the photocharges transmitted through the transmission transistor T1. The photocharges accumulated during the effective exposure period may be stored in the floating diffusion node capacitor $C_{FD}$ of the FD node.

The floating diffusion node capacitor $C_{FD}$ may be implemented by adding a capacitor to the FD node, or a parasite capacitor of the FD node may be utilized as the floating diffusion node capacitor $C_{FD}$. If the parasite capacitor is used as the floating diffusion node capacitor, additional hardware may not be needed.

The reset transistor R discharges the photocharges accumulated on the FD node.

The source follower (SF) transistor amplifies and converts the photocharge in the floating diffusion node capacitor $C_{FD}$ into a voltage signal.

The selection transistor S outputs an output voltage selectively according to a row selection signal ROW_SEL. The operation of the pixel 700 is further described with reference to FIG. 8.

Figure 8:
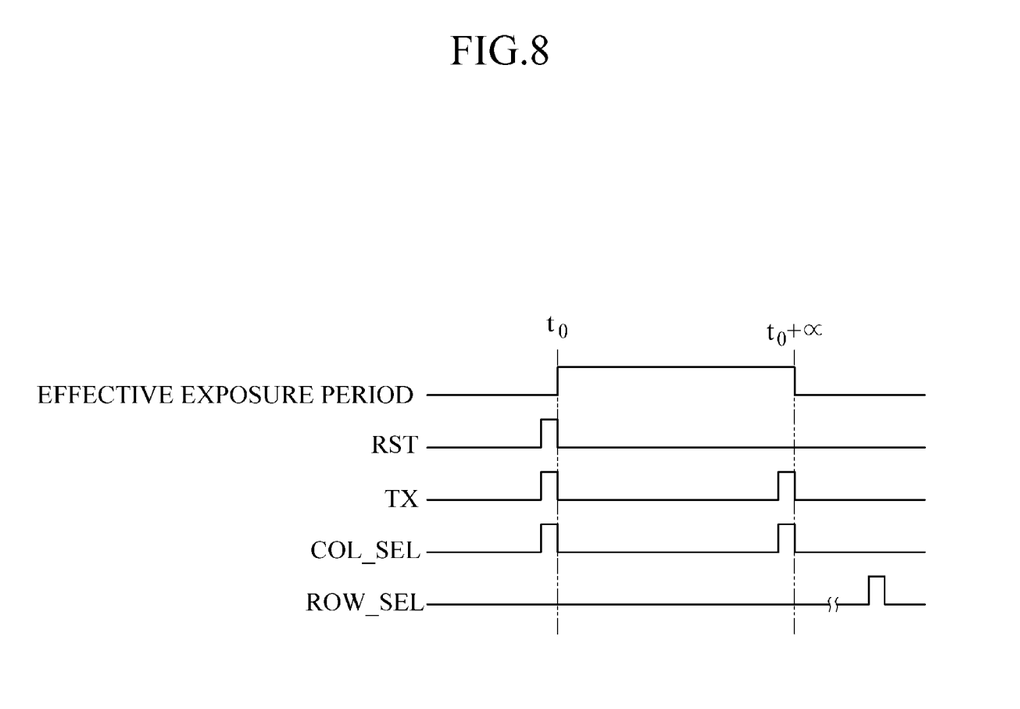
FIG. 8 is an example of a timing diagram with respect to an operation of a pixel.

FIG. 8 illustrates an example of a timing diagram with respect to an operation of a pixel. The pixel 700 is positioned at a location where X-ray radiation arrives without scattering, as shown in FIG. 8, during the effective exposure period for which the pixel 700 is exposed to a beam of primary radiation. Although FIG. 8 illustrates a timing diagram with respect to the operation of one pixel, a plurality of pixels which are simultaneously exposed to the X-ray radiation may be operated according to the same timing as the pixel of FIG. 8.

Before the X-ray exposure start time $t_0$, a column selection signal COL_SEL connected to a drain end of the transmission control transistor T2, a gate signal TX of the transmission control transistor T2, and a reset signal RST are set to an increased level. Accordingly, the photocharges accumulated on the photodiode PD and the FD node are discharged such that the photodiode PD and the FD node are initialized. For example, the accumulated photocharges may be discharged through a drain end of the reset transistor R.

Between the X-ray exposure start time $t_0$ and the X-ray exposure end time $t_0+\alpha$, the photocharges according to the effective exposure to the X-ray radiation are accumulated on the photodiode PD.

At the X-ray exposure end time $t_0+\alpha$, the gate signal TX of the transmission control transistor T2 and the column selection signal COL_SEL are set to an increased level such that the photocharges accumulated in the photodiode PD are transmitted to the FD node. The FD node stores the photocharges accumulated during the effective exposure period. The accumulated photocharges are retained in the FD node until signals corresponding to the photocharges are output in response to an application of the row selection signal ROW_SEL. For example, the row selection signal ROW_SEL may be applied when the scanning of the object 10 is completed, when the scanning of a predetermined area is completed, or at preset time intervals.

While the example pixel included in the detector 140 is implemented as a CMOS transistor in the above description, other devices capable of detecting X-ray radiation may be used, for example, a thin film transistor (TFT), a photon counting detector, and the like. Such an X-ray detecting device may be configured to accumulate and store photocharges in an existing pixel during an X-ray exposure period and output signals corresponding to the accumulated photocharges each time a predetermined area of a subject is scanned or when the entire area of the subject is completely scanned. In another example, unlike a photocharge accumulating detector, a two-dimensional array photon counting detector includes a counter circuit in a pixel, and thus can be configured to implement an exposure control function by turning on the counter only during an effective exposure period.

Figure 9:
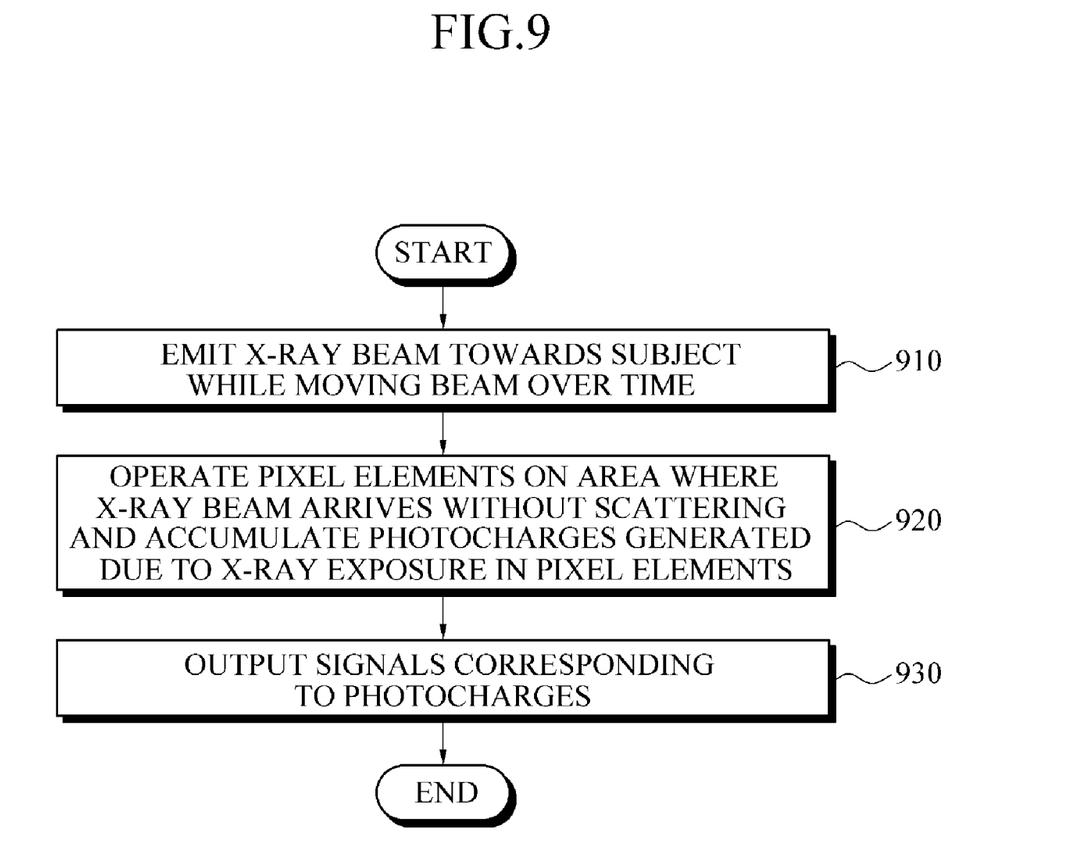
FIG. 9 is a flowchart illustrating an example of an X-ray imaging method.

Hereinafter, an X-ray imaging method is described with reference to FIG. 9 in conjunction with FIG. 1. FIG. 9 illustrates an example of an X-ray imaging method.

The X-ray imaging apparatus 100 emits an X-ray beam onto the subject 10 while moving the X-ray beam over time in operation 910. At least two or more X-ray beams may be emitted to the subject 10 to reduce the scanning time.

The X-ray imaging apparatus 100 may only operates pixels positioned at an exposure area where the X-ray beam arrives without scattering and may accumulate photocharges generated due to the X-ray radiation exposure in the pixels over time in operation 920. The photocharges accumulated in the pixels may be retained in the pixels until signals corresponding to the photocharges are output.

The X-ray imaging apparatus 100 outputs signals corresponding to the photocharges in operation 930. The output of the signals corresponding to the photocharges may be performed when the scanning of the subject 10 is completed or when the scanning of a predetermined area of the subject 10 is completed. In addition, the X-ray imaging apparatus 100 may generate an image using the output signals.

The processes, functions, methods and/or software described above may be recorded, stored, or fixed in one or more computer-readable storage media that includes program instructions to be implemented by a computer to cause a processor to execute or perform the program instructions. The media may also include, alone or in combination with the program instructions, data files, data structures, and the like. The media and program instructions may be those specially designed and constructed, or they may be of the kind well-known and available to those having skill in the computer software arts. Examples of computer-readable media include magnetic media, such as hard disks, floppy disks, and magnetic tape; optical media such as CD-ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

The term "pixel," as used herein, refers to a photo-element unit cell containing at least a photosensor for converting photons to electrical changes. A CMOS imaging device was described for convenience; however, embodiments have wider applicability to other pixels of other imaging devices. In addition, the detector or photosensor of each pixel may be implemented, as nonlimiting examples only, as a pinned photodiode, a p-n junction photodiode, a Schottky photodiode, a photogate, or any other suitable photoconversion device or device that may accumulate and/or store photocharges.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An X-ray imaging apparatus comprising:
an X-ray source configured to emit X-rays;
a collimator configured to collimate X-rays into an X-ray beam;
a detector comprising a two-dimensional array of pixels configured to accumulate and store photocharges; and
a controller configured to:
control the collimator such that the X-ray beam scans a subject while moving over time; and
control the detector to only operate pixels at an exposure area of the detector at which the X-ray beam arrives and to turn off or keep off pixels at a remaining area of the detector excluding the exposure area to reduce scattering, such that photocharges generated due to X-ray exposure are accumulated and stored in the pixels.

2. The X-ray imaging apparatus of claim 1, wherein the controller is further configured to control the detector to output signals corresponding to the photocharges stored in the pixels, in response to scanning of the subject or a predetermined area of the subject being completed.

3. The X-ray imaging apparatus of claim 1, wherein the controller comprises an image processor configured to generate an image by processing signals corresponding to the photocharges accumulated in the detector.

4. The X-ray imaging apparatus of claim 1, wherein the accumulated photocharges are retained in the pixels until signals corresponding to the accumulated photocharges are output.

5. The X-ray imaging apparatus of claim 1, wherein the detector comprises a complementary metal-oxide semiconductor (CMOS) image device.

6. The X-ray imaging apparatus of claim 5, wherein each pixel comprises:
a photodiode configured to:
receive the X-ray beam; and
generate the photocharge;
a transmission transistor that is connected to the photodiode and configured to transmit the photocharge;
a transmission control transistor configured to control the transmission transistor;
a floating diffusion node configured to receive the photocharge through the transmission transistor;
a reset transistor configured to discharge the photocharge accumulated in the floating diffusion node;
a source follower transistor that amplifies and converts the photocharge in the floating diffusion node into a voltage signal; and
a selection transistor configured to selectively output the voltage signal.

7. The X-ray imaging apparatus of claim 6, wherein, in each pixel:
a column selection signal connected to a drain end of the transmission control transistor, a gate signal of the transmission control transistor, and a reset signal applied to the reset transistor are set to an increased level such that photocharges accumulated in the photodiode and the floating diffusion node are discharged immediately before exposure to the X-ray radiation starts; and
the gate signal of the transmission control transistor and the column selection signal are set to an increased level such that the photocharge accumulated in the photodiode is transferred to the floating diffusion node at end of exposure to the X-ray radiation.

8. The X-ray imaging apparatus of claim 1, wherein:
the detector comprises a sensor configured to recognize an X-ray arrival location in real-time; and
the controller is further configured to operate pixels positioned at the X-ray arrival location based on the recognized X-ray arrival location.

9. The X-ray imaging apparatus of claim 1, wherein two or more X-ray beams are simultaneously emitted towards the subject.

10. An X-ray imaging method, comprising:
radiating an X-ray beam towards a subject while moving the X-ray beam over time;
operating pixels in an exposure area of a detector where the X-ray beam arrives and turning off or keeping off pixels at a remaining area of the detector excluding the exposure area to reduce scattering;
accumulating photocharges generated due to X-ray radiation exposure in the pixels over time; and
outputting signals corresponding to the photocharges.

11. The X-ray imaging method of claim 10, wherein the outputting of the signals corresponding to the photocharges is performed, in response to scanning of the subject or a predetermined area of the subject being completed.

12. The X-ray imaging method of claim 10, further comprising generating an image using the output signals.

13. The X-ray imaging method of claim 10, wherein the accumulating photocharges comprises retaining the photocharges in the pixels until image signals corresponding to the photocharges are output.

14. The X-ray imaging method of claim 10, wherein the radiating comprises radiating two or more X-ray beams simultaneously towards the subject.

15. A controller for controlling an imaging apparatus, the controller comprising:
a source controller configured to control a source to emit a source beam from a start point to an end point to obtain information about a subject;
an exposure controller configured to selectively control a detector comprising an array of pixels configured to accumulate and store photocharges over time corresponding to the emitted source beam to obtain information about the subject; and
a synchronization controller configured to synchronize the source controller and the exposure controller such that only a portion of pixels where the source beam arrives at the detector are driven as the source beam moves from the start point to the end point,
wherein the exposure controller is further configured to control the detector such that only the portion of the pixels detect the source beam at the same time and remaining pixels excluding the portion of pixels are turned off or kept off.

16. The controller of claim 15, further comprising a collimator controller configured to control movement of a collimator disposed between the source and the detector such that the movement of the collimator is synchronized with the movement of the source beam.

17. The controller of claim 15, wherein the exposure controller is further configured to control a sensor of the detector to sense location information about a location on the array of pixels where the source beam arrives at the detector, in real time.

18. The controller of claim 17, wherein the synchronization controller is further configured to synchronize the source controller and the exposure controller based on the sensed location information.

19. The controller of claim 15, wherein the synchronization controller is further configured to control the exposure controller to predict the location at which the source beam arrives over time.

* * * * *